United States Patent [19]
Lowski et al.

[11] 4,146,400
[45] Mar. 27, 1979

[54] COLOR PHOTOGRAPHIC MATERIAL CONTAINING NEW 2-EQUIVALENT YELLOW COUPLERS

[75] Inventors: Dieter Lowski, Bergheim, Erft; Karl-Wilhelm Schranz, Odenthal-Hahnenberg; Erich Wolff, Leverkusen, all of Fed. Rep. of Germany

[73] Assignee: AGFA-Gevaert AG, Leverkusen, Fed. Rep. of Germany

[21] Appl. No.: 830,591

[22] Filed: Sep. 6, 1977

[30] Foreign Application Priority Data

Sep. 9, 1976 [DE] Fed. Rep. of Germany ....... 2640601

[51] Int. Cl.$^2$ ................................................ G03C 1/40
[52] U.S. Cl. ................................. 96/100 R; 96/100 N
[58] Field of Search ........................ 96/100, 55, 56.5

[56] References Cited

U.S. PATENT DOCUMENTS

| | | |
|---|---|---|
| 3,700,454 | 10/1972 | Sakamoto et al. ............ 96/100 |
| 3,880,658 | 4/1975 | Lestina et al. ............... 96/100 |
| 4,021,248 | 5/1977 | Shiba et al. .................. 96/55 |

*Primary Examiner*—J. Travis Brown
*Attorney, Agent, or Firm*—Connolly and Hutz

[57] ABSTRACT

New 2-equivalent yellow couplers of the structure

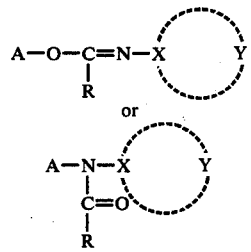

in which X represents a ring member selected from N and C; Y completes a 5-, 6- or 7-membered nitrogen-containing ring; R represents alkyl, aryl, alkoxy or heterocyclic ring; and A represent a yellow coupler radical provide high maximum color densities together with low fog on storage under humid conditions.

3 Claims, No Drawings

COLOR PHOTOGRAPHIC MATERIAL CONTAINING NEW 2-EQUIVALENT YELLOW COUPLERS

This invention relates to new 2-equivalent yellow couplers and to their use in colour photographic materials.

For the production of coloured photographic images, it is known to develop the exposed silver halide of a light sensitive silver halide emulsion layer with an aromatic developer substance containing at least one primary amino group in the presence of colour couplers. The colour couplers react with the oxidised colour developer to form an image dye in accordance with the silver image present.

Subtractive three-colour photography is generally carried out with a multilayered light sensitive photographic material containing a red sensitised, a green sensitised and a blue sensitive silver halide emulsion layer, from which a cyan, a magenta and a yellow dye image are formed by colour development in the presence of suitable colour couplers.

The couplers used for forming the cyan dyes are usually phenols or naphthols, the couplers for forming the magenta dyes are usually pyrazolones and the couplers used for forming the yellow dye are usually open-chain compounds which contain a methylene group with two carbonyl groups attached thereto. The dyes formed by the coupling reaction are azomethines, indamines or indophenols, depending on the structure of the coupler and of the developer.

Conventional yellow couplers contain an active methylene group which reacts with the oxidised colour developer in the process of colour development. This reaction requires four equivalents of developable silver halide and these couplers are therefore known as 4-equivalent couplers. Other couplers are known which contain a methylene group in which one hydrogen atom is substituted by a group which is split off in the coupling reaction. In this case, only two equivalents of developable silver halide are required for forming the dye and these couplers are therefore known as 2-equivalent couplers. The following are examples of the groups which can be split off in the reaction: halogen, alkoxy or aroxy, thioether groups and saturated or unsaturated heterocyclic rings which are attached to the coupling position through a ring nitrogen atom and in most cases contain ketogroups.

The advantage of 2-equivalent couplers compared with 4-equivalent couplers is that the quantity of silver halide required to form a given quantity of dye is approximately only half of the quantity required with 4-equivalent couplers. Apart from the saving in silver, this means that the emulsion layer can be cast more thinly so that improved resolution and sharpness of the photographic material can be obtained.

Among the 2-equivalent yellow couplers known in the art containing the above mentioned groups which can be split off, those which contain halogen as a substituent which is split off have proved to be particularly suitable in practice because the reactivity of the 2-equivalent yellow coupler used in colour development of a photographic material must be sufficiently high to ensure that adequate colour densities are obtained even with short processing times.

However, 2-equivalent yellow couplers containing fluorine as removable group have failed to become established in practice due to difficulties in preparation while 2-equivalent yellow couplers containing chlorine as removable group frequently have a harmful effect on the photographic properties of the silver halide emulsion. As has been described in German Offenlegungsschrift No. 2,114,577, the only yellow couplers containing chlorine as removable group which are photographically relatively inert and have only a slight effect on the formation of colour fog during development are certain yellow couplers based on benzoyl acetanilide, but even these couplers do not satisfy the photographic requirements in all respects since an increase in fogging during development cannot be completely excluded if the unprocessed photographic material has been stored under moist, warm conditions.

There has been no lack of attempts in practice to find new 2-equivalent yellow couplers which are easily prepared and sufficiently reactive for colour photographic development. The known 2-equivalent yellow couplers, however, do not as yet fulfil these requirements.

A further problem lies in the difficulty of introducing 2-equivalent couplers in a finely divided form into the hydrophilic colloid layers of photographic materials in such a manner that they will be stable and will not crystallise from the hydrophilic colloid layers or in any other way deleteriously affect the photographic or mechanical properties of the layers.

Furthermore, 2-equivalent couplers must be sufficiently stable to withstand prolonged storage of the photographic material at elevated temperature or under moist, warm conditions so that the releasable group will not be split off before chromogenic development. At the same time, this group must be capable of being readily and completely split off by chromogenic development if high colour saturation and sufficiently high sensitivity are to be achieved. These properties must, of course, be independent of the manner in which the couplers are introduced into the hydrophilic colloid layers. Diffusion resistant hydrophobic couplers are generally rendered soluble in alkalis by the introduction of solubilising groups and introduced into the layer in this form or they are dissolved in an organic solvent and incorporated in the gelatine solution in known manner by emulsification, optionally with the addition of oily coupler solvents.

The reactivity of the couplers depends to a certain extent on the method used for preparing the emulsion. In order to obtain sufficiently high reactivity of the 2-equivalent couplers, the hydrophilic colloid layer and/or the more hydrophobic oil droplets must be capable of exerting a positive influence on the removal of the releasable group during chromogenic development by a solvating effect.

The releasable group must, of course, be photographically inert and must not have any deleterious effect on the dyes formed in the reaction nor on the stability of unused residual coupler in the layer.

It is an object of the present invention to provide new 2-equivalent yellow couplers which are easily prepared and which are suitable for use in the light sensitive materials for building up the yellow partial images and superior in their properties to the known art couplers.

This invention therefore provides a light sensitive material comprising at least one silver halide emulsion layer and in close special relation thereto, a diffusion resistant 2-equivalent yellow coupler of one of the following formulae:

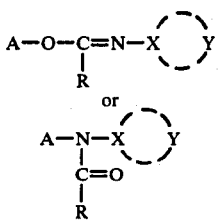 (I)

or (II)

in which formulae:

X represents a ring nitrogen or ring carbon atom;

Y represents the ring members required to complete a saturated or unsaturated 5-, 6- or 7-membered heterocyclic ring which contains nitrogen and may have other carbocyclic or heterocyclic rings condensed to it, for example thiadiazole, 1,2,3- or 1,2,4-triazole, tetrazole, thiazole, 1,2- or 1,3-diazole, pyrrole, triazine, pyridine or pyrimidine; these heterocyclic groups may contain further substituents, e.g. alkyl, alkoxy, halogen, in particular chlorine, or nitro; they may also contain keto-groups on the ring.

R represents
(1) an aliphatic group, in particular an aliphatic group having up to five carbon atoms, preferably an alkyl group which aliphatic group may be substituted, e.g. with alkoxy, with halogen, preferably chlorine, or with phenyl;
(2) an aryl group, in particular a phenyl or naphthyl group, which aryl group may be substituted, e.g. with alkyl, alkoxy, halogen, nitro, cyano, trifluoromethyl, alkyl, aroxy or aryl sulphonyl;
(3) an alkoxy group, preferably with up to 5 atoms, or
(4) a heterocyclic group, e.g. a furyl or pyridyl group;

A represents the radical of a yellow coupler molecule containing the removable group in the coupling position, e.g. of the following formula:

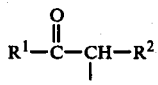

in which
$R^1$ represents
(1) an alkyl group with preferably 1 to 32 carbon atoms which may be substituted, in particular a branched alkyl group in which a secondary or tertiary carbon atom is preferably attached directly to the carbonyl group, in particular a tertiary butyl group;
(2) an alkoxy alkyl group;
(3) a cycloalkyl group;
(4) a heterocyclic group or
(5) an aryl group in particular a phenyl group, which may be substituted with one or more substituents, e.g. with halogen, alkoxy or acylamino, alkyl, aroxy, hydroxy, alkylamino or dialkylamino;

$R^2$ represents cyano or a group of the formula

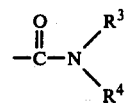

in which
$R^3$ represents an alkyl group preferably containing 1 to 4 carbon atoms or, preferably, hydrogen;
$R^4$ represents
(1) an alkyl with 1 to 18 carbon atoms or preferably
(2) an aryl group, in particular a phenyl group, which may be substituted with one or more groups which may be the same or different, e.g. with alkyl groups having from 1 to 18 carbon atoms; an aryl group, e.g. phenyl; an aralkyl group, e.g. benzyl; an aroxy group, e.g. phenoxy; or, in particular, halogen, e.g. chlorine or bromine or a sulpho, carboxyl, acyl, acyloxy or acylamino group, the above mentioned acyl groups being optionally derived from aliphatic or aromatic carboxylic or sulphonic acids inclusive of carbonic acid monoesters and carbamic or sulfamic acids which may be substituted by the same or different alkyl, aryl, aralkyl or heterocyclic groups.

By suitable choice of the substituents $R^1$ and $R^4$, the yellow couplers according to the invention may be equipped with at least one group which confers diffusion resistance, e.g. a straight or branched chain alkyl group having from 10 to 18 carbon atoms, or they may be substituted with alkyl substituted phenoxy groups which may be attached either directly or indirectly to the optionally aromatic groups $R^1$ or $R^4$, for example by way of —O—; —S—; —CONH—; —NHCO—; —SO$_2$NH—; —NHSO$_2$— or other intermediate links. If the coupler is desired to be soluble in alkalis, at least one of the groups $R^1$ and $R^4$ may carry groups which confer solubility in alkalis, preferably sulpho groups. Examples of suitable yellow couplers according to the invention are given below:

1)

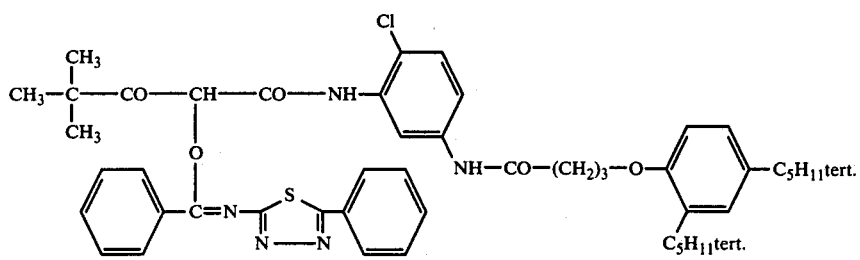

-continued
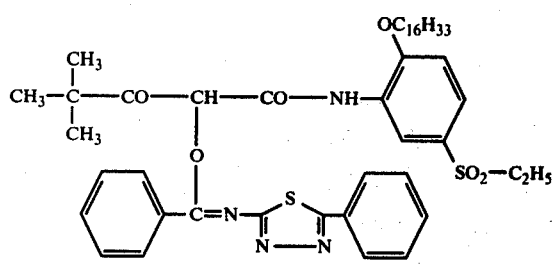
2)
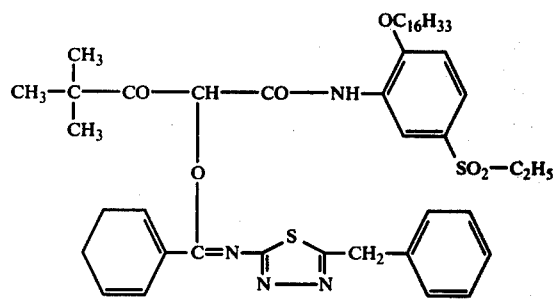
3)
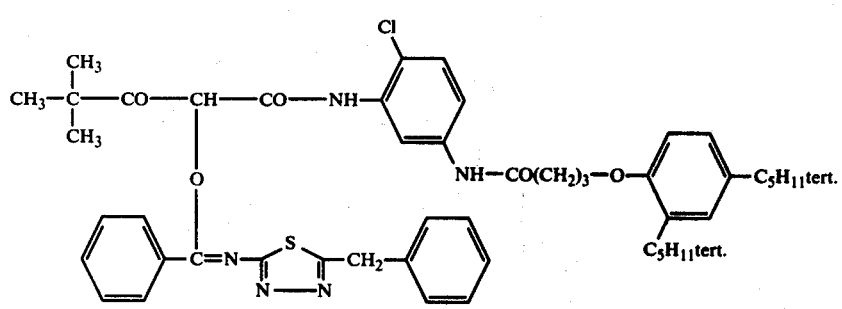
4)
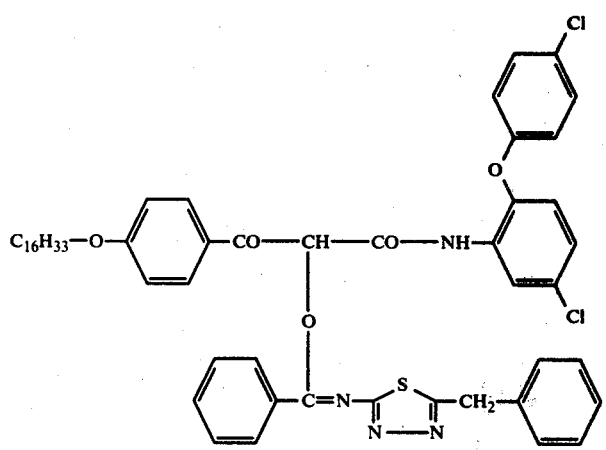
5)
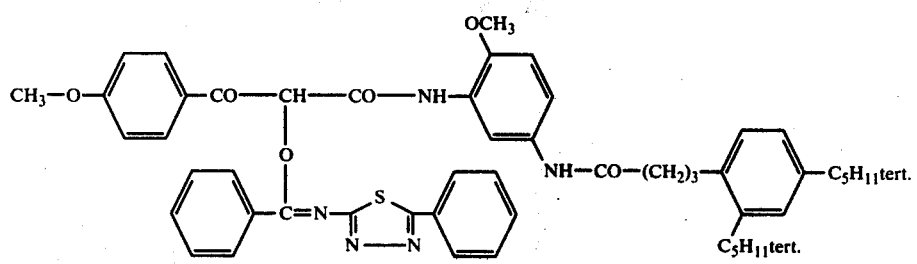
6)

7)
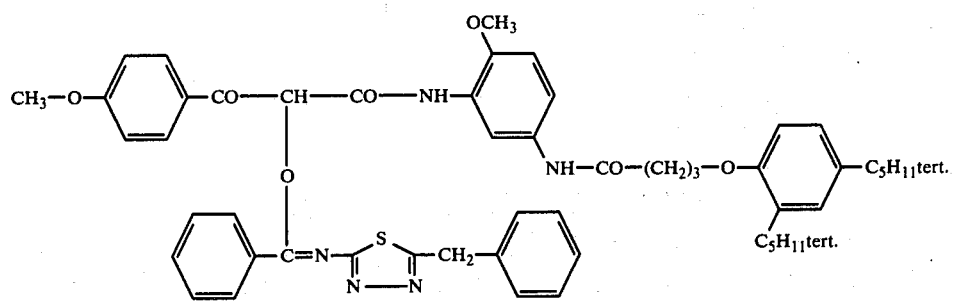
8)
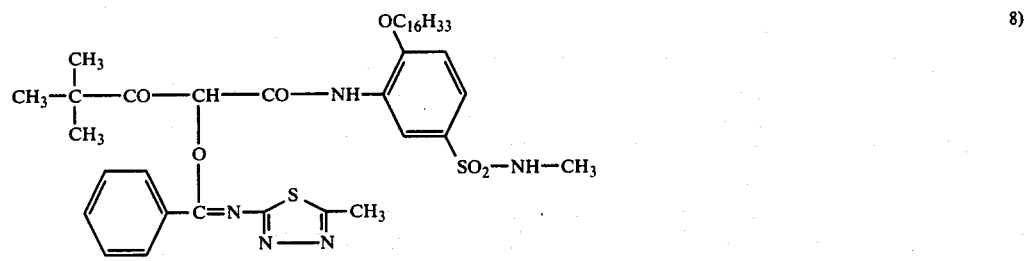
9)
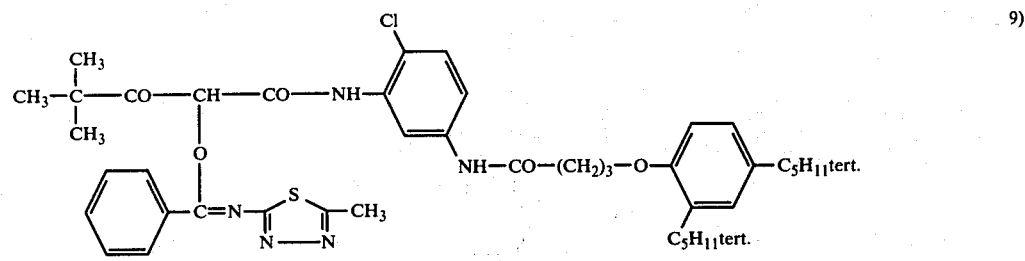
10)
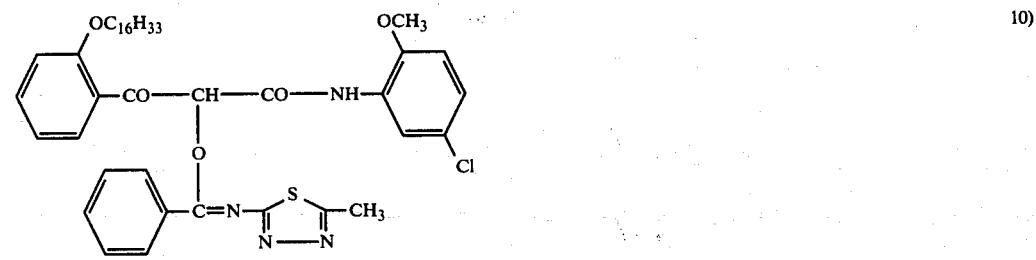
11)
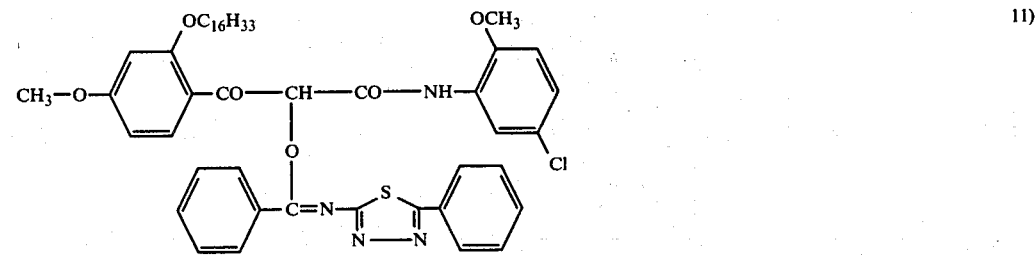
12)
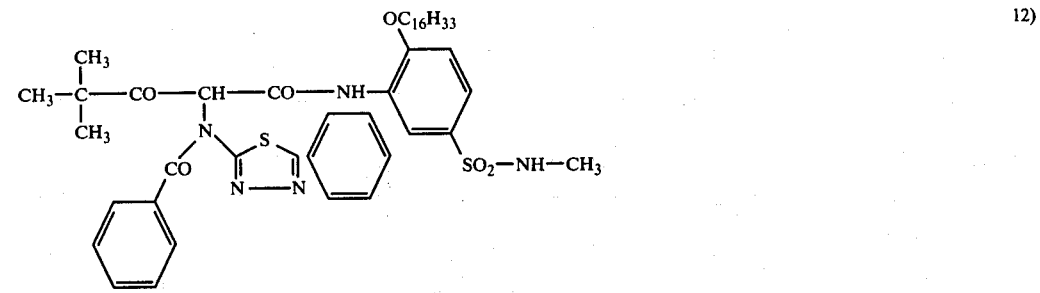

-continued
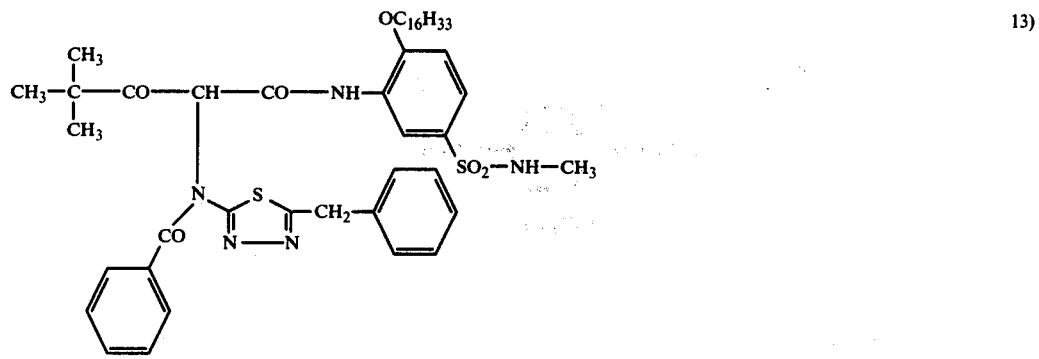
13)
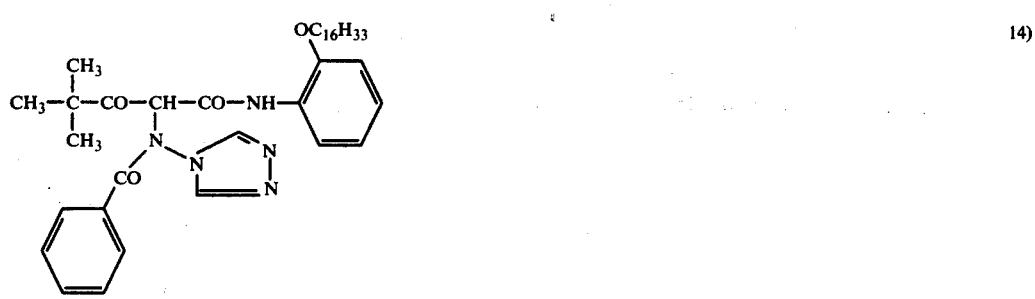
14)
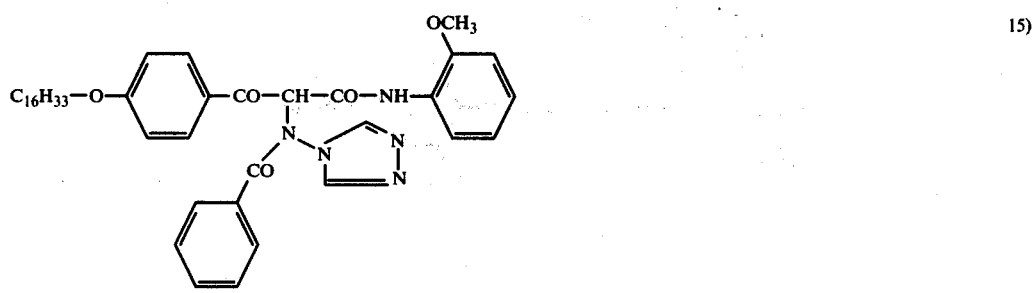
15)
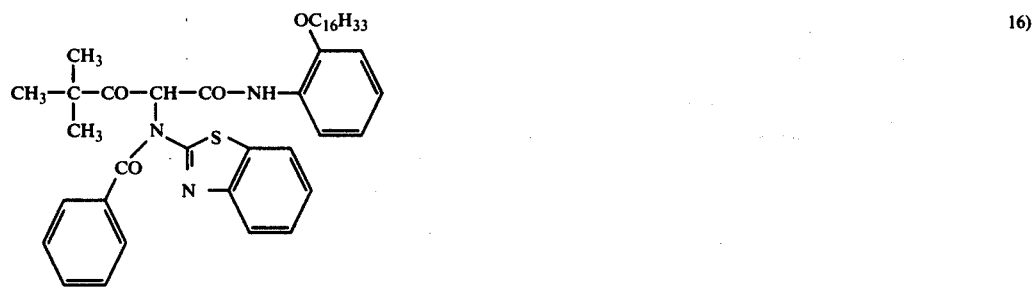
16)
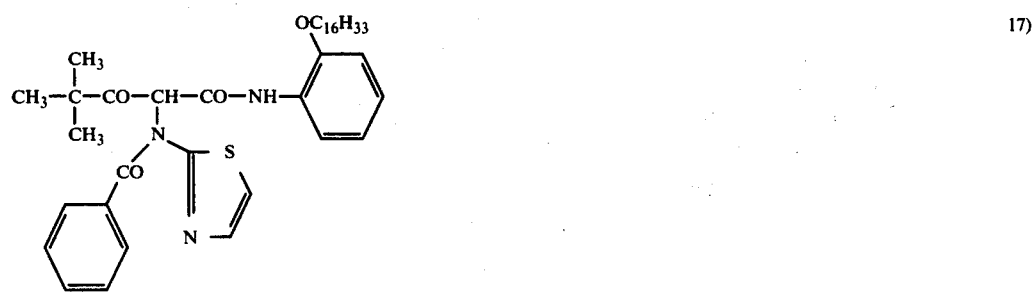
17)

-continued
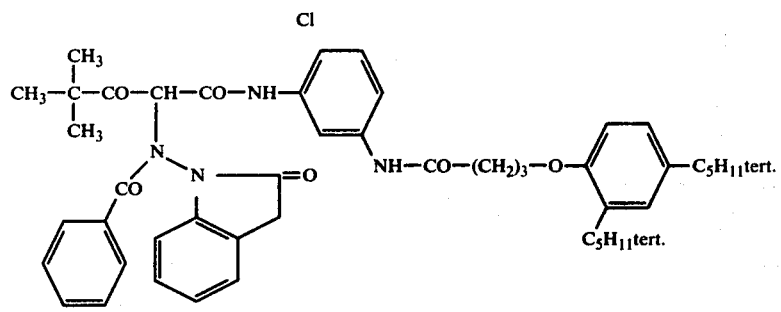
18)
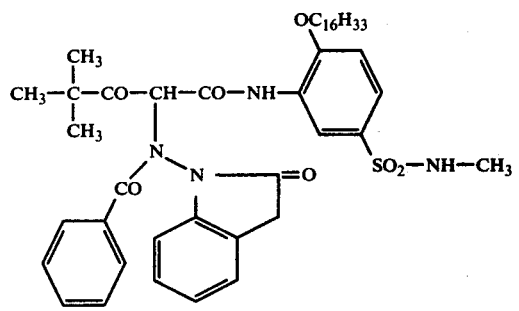
19)
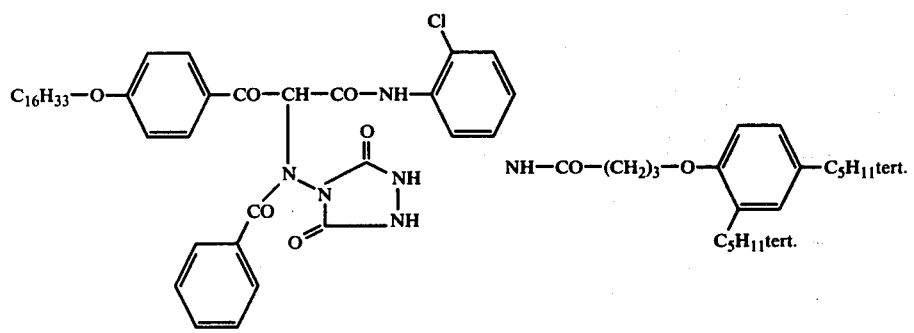
20)
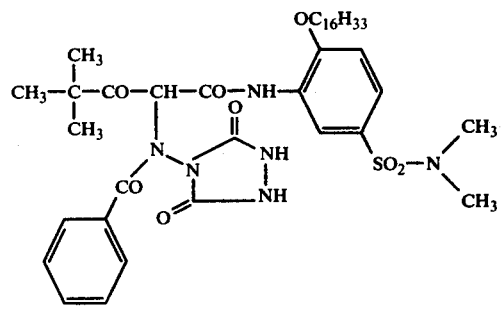
21)
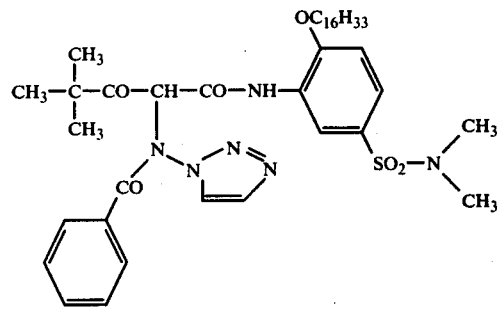
22)

-continued

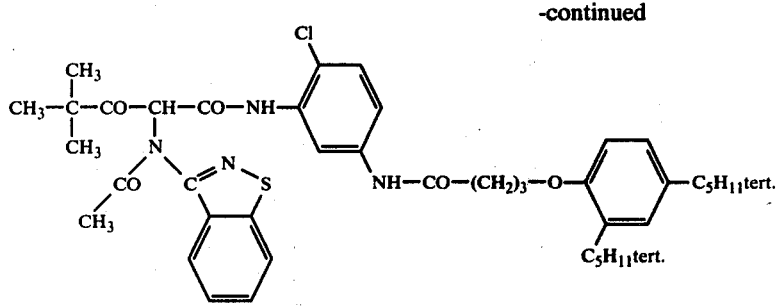

23)

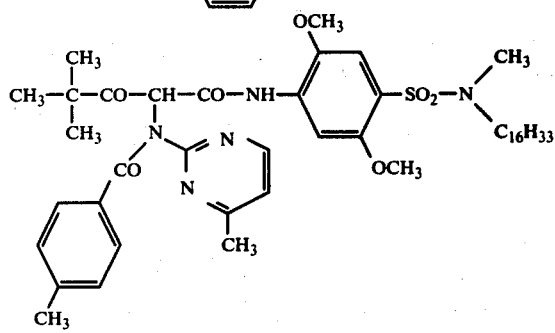

24)

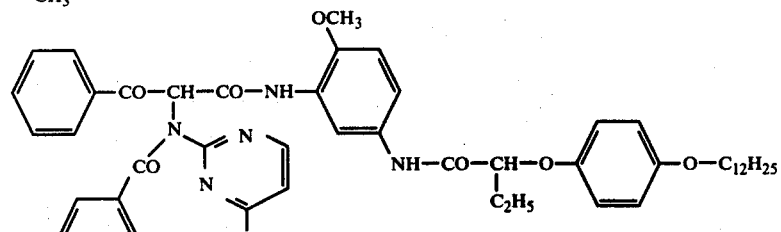

25)

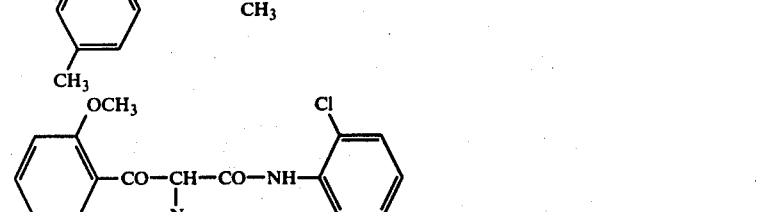

26)

The preparation of some yellow couplers according to the invention is described in detail below.

The yellow couplers according to the invention can be prepared from the corresponding 2-equivalent couplers containing chlorine or bromine as releasable substituent by reaction with a heterocyclic compound of the following formula (III)

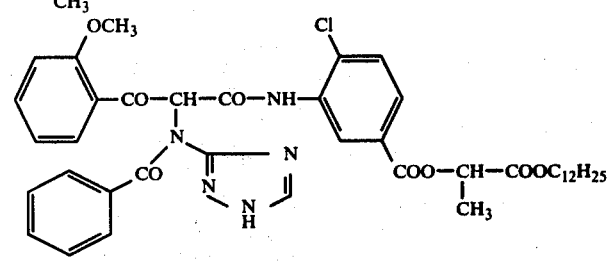   (III)

in which X, Y and R have the meanings already specified and in which M represents a metal ion, e.g. an ion of sodium, potassium, silver, calcium or magnesium or a quaternary ammonium ion, e.g.

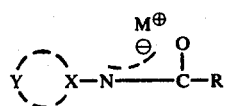

in the presence of a base in the usual manner, for example as described in German Offenlegungsschrift No. 2,213,461. The reaction may be carried out in an aprotic solvent but is preferably carried out in a polar solvent such as acetonitrile, methyl formamide or acetone or in benzene. Suitable basic compounds include open-chain or cyclic amines such as pyridine or alkali metal salts or alcoholates such as sodium alcoholate.

The reaction also proceeds very favourably if, as described in German Offenlegungsschrift No. 2,329,587, hexamethyl phosphoric acid triamide is used as solvent, since this solvent has the added effect of accelerating the reaction.

When the coupler molecular indicated above and the anion shown in formula (III) are reacted together, substitution may take place either on the nitrogen or the oxygen atoms, depending on the reaction conditions and upon the ambident character (resonance structure) of the anion. In some cases, the two products may be formed side-by-side. The amident character is illustrated by the following formulae:

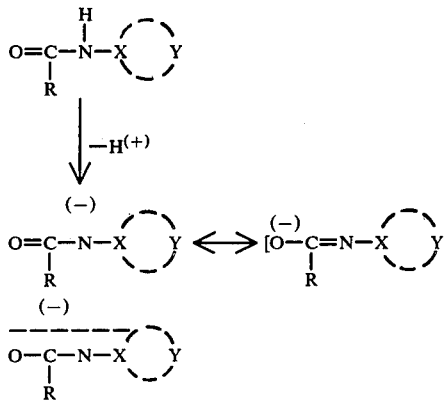

The yellow couplers according the the invention can therefore also be clearly defined by saying that they split off the releasable group of the above anionic formula in their reaction with the oxidation product of the colour developer.

The α-Cl-substituted couplers and α-Br-substituted couplers may be prepared by the methods described in U.S. Pat. No. 2,728,658 or by the reaction of an α-unsubstituted compound with N-bromo succinimide.

The couplers according to the invention may also be prepared from 4-equivalent couplers by the one stage synthesis described in German Offenlegungsschrift No. 2,545,756.

The preparation of some couplers is described below. The other couplers according to the invention may be prepared in a similar manner.

Coupler No. 9

20 g of α-pivaloyl-α-chloro-2-chloro-5-(γ-(2,4-di-tert. amyl phenoxy)-butyramido)-acetanilide are heated to boiling with
9 g of 2-benzoylamino-5-methyl-thiadiazole and
20 ml of triethylamine in
120 ml of acetonitrile.

After about 30 minutes, the reaction mixture is stirred into ice/HCl, suction filtered, washed with water and dried on clay. The crude product is recrystallised from alcohol, suction filtered and washed with a small quantity of cold alcohol.

Yield: 9.5 g m.p.: 135° to 138° C.

Coupler No. 8

20 g of α-pivaloyl-α-chloro-2-cetyloxy-5-N-methyl-sulfphamoylacetanilide are heated to boiling with
10 g of 2-benzoylamino-5-methyl-thiadiazole and
20 ml of triethylamine in
120 ml of acetonitrile.

After 30 minutes, the reaction mixture is cooled and suction filtered to remove unreacted thiadiazole derivative and the filtrate is stirred into ice/HCl. The filtrate is taken up in ether and the ethereal solution is dried over sodium sulfphate and filtered. Petroleum ether is added to the filtered solution which is then cooled. The precipitated crude product is washed with a little cold ether/petroleum ether and then reprecipitated from ether/petroleum ether.

Yield: 10.5 g, m.p.; 172° to 175° C.

Coupler No. 5

20 g of α-4-cetyloxybenzoyl-α-chloro-(2'-p-chlorophenoxy-5'-chloro)-acetanilide are heated to boiling with
13 g of 2-benzoylamino-5-benzyl-thiadiazole and
20 ml of triethylamine in
120 ml of acetonitrile for one hour.

The reaction mixture is then stirred into ice/HCl, suction filtered and washed with water. The crude product is dissolved hot in ligroin and filtered from unreacted thiadiazole compound. The crystals which precipitate on cooling are washed with a little ligroin. For further purification, they are suspended in hot methanol, suction filtered and washed with methanol.

Yield: 16 g m.p.: 122° to 124° C.

Coupler No. 2

25 g of α-pivaloyl-α-chloro-(2'-cetyloxy-5'-ethylsulphonyl)acetanilide are dissolved in
130 ml of hexamethylphosphoric acid triamide.
19 g of 2-benzoylamino-5-phenyl-thiadiazole and
5 g of sodium methylate (95%) are added portionwise to the resulting solution.

When the reaction has been completed, the reaction mixture is stirred into ice/HCl, suction filtered, washed with water and dried. The crude component is dissolved hot in ethyl acetate, clarified with active charcoal and then suction filtered when cooled. It is then recrystallised once from alcohol and once from ether/methanol.

Yield: 14.6 g, m.p.: 100° to 102° C.

The light-sensitive photographic material of the present invention contains the new 2-equivalent yellow couplers in close special relationship to a silver halide emulsion layer. This means that the coupler is either in the silver halide emulsion layer or in proximity thereto so that the oxidation product of the color developer formed in the silver halide layer can easily come into effective contact with the coupler. For this purpose the coupler may also be incorporated in a non light-sensitive binder layer adjacent to the silver halide layer.

In the preparation of the light sensitive colour photographic materials according to the invention, the diffusion-resistant yellow couplers may be incorporated in known manner in the casting solution of the silver halide emulsion layers or of other colloid layers. For example, water soluble colour couplers, that is to say those which contain one or more groups which confer solubility in water, such as sulphur or carboxyl groups, in the acid or salt form, may be added to a hydrophilic casting solution from an aqueous solution whereas colour couplers which are insoluble in water or insufficiently water soluble may be added to such a hydrophilic casting solution from a solution in suitable water miscible or water immiscible, high boiling or low boiling organic solvents or mixtures of such solvents, optionally in the presence of a wetting agent or dispersing agent, said hydrophilic casting solution constituting the whole or only a part of the binder of the photographic colloid layer or emulsion layer. The hydrophilic casting solution may, of course, contain other of the usual additives in addition to the binder. The water insoluble colour couplers which contain fluorosulphonyl groups or carboxylic acid ester groups such as ethoxy carbonyl groups may also be converted into the corresponding sulphonic acids or carboxylic acids or alkali metal salts thereof by alkaline hydrolysis and then added from aqueous solutions.

The solution of colour coupler need not be directly dispersed or dissolved in the casting solution of the silver halide emulsion layer or other water permeable layer. It may advantageously first be dissolved or dispersed in an aqueous, light insensitive solution of a hydrophilic colloid and then, optionally after removal of the organic solvent, it may be mixed with the casting solution for the light sensitive silver halide emulsion layer or the casting solution of some other water permeable layer before it is applied. Further details about suitable techniques for incorporating colour couplers in hydrophilic colloid layers of a photographic material may be found in published Dutch Patent Applications Nos. 6,516,423; 6,516,424; 6,600,098; 6,600,099 and 6,600,628; Belgian Patent Specification No. 750,889; U.S. Patent No. 2,304,940 and British Pat. No. 791,219.

To produce photographic colour images, an exposed silver halide emulsion layer is developed with an aromatic primary amino developer substance in the presence of a colour coupler according to the invention. The developer substance used may be any colour developer substance which, in the form of its oxidation product, is capable of reacting with the colour coupler to form an azomethine dye. Suitable developer substances include aromatic compounds such as p-phenylene diamine and its derivatives, for example N,N-dialkyl-p-phenylene diamines such as N,N-diethyl-p-phenylene diamine, N,N-dimethyl-p-phenylenediamine, N,N-diethyl-p-phenylenediamine, N-monomethyl-p-phenylenediamine, 2-amino-5-diethylaminotoluene, N-butyl-N-$\omega$-sulfobutyl-p-phenylenediamine, 2-amino-5-(N-ethyl-N-$\beta$-methanesulfonamidoethylamino)-toluene and the like. Other suitable color developers have been described, for example, in J. Amer. Chem. Soc. 73, 3100–3125 (1951).

The light-sensitive silver halide emulsions used may be emulsions of silver chloride, silver bromide or mixtures thereof, which may have a silver iodide content of up to 10 mol-%, in one of the usual hydrophilic binders. The binder used for the photographic layer is preferably gelatine but this may be partly or completely replaced by other natural or synthetic binders. Examples of suitable natural binders include alginic acid and its derivatives such as salts, esters or amides, cellulose derivatives such as carboxymethyl cellulose, alkyl celluloses such as hydroxyethyl cellulose, starch or its derivatives such as ethers or esters, or carageenates. Suitable synthetic binders include polyvinyl alcohol, partially saponified polyvinyl acetate and polyvinyl pyrrolidone.

The emulsions may also be chemically sensitised, for example by adding sulfur compounds such as allyl isothiocyanate, allyl thiourea or sodium thiosulfate during chemical ripening. Reducing agents may also be used as chemical sensitisers, for example the tin compounds described in Belgian Patent Specifications No. 493,464 and 568,687, or polyamines such as diethylene triamine or aminomethane sulfinic acid derivatives, e.g. according to Belgian Patent Specification No. 547,323.

Noble metals such as gold, platinum, palladium, iridium, ruthenium or rhodium and compounds of these metals may also be used as chemical sensitisers. This method of chemical sensitisation has been described in the article by R. KOSLOWSKY, Z. Wiss. Phot. 46, 65–72 (1951). The chemical sensitisers mentioned above may also be used in combination with each other.

The emulsions may also be sensitised with polyalkylene oxide derivatives, for example with a polyethylene oxide having a molecular weight of between 1.000 and 20.000, or with condensation products of alkylene oxides and aliphatic alcohols, glycols or cyclic dehydration products of hexitols with alkyl substituted phenols, aliphatic carboxylic acids, aliphatic amines, aliphatic diamines and amides.

The condensation products have a molecular weight of at least 700 and preferably more than 1.000. These sensitisers may, of course, be used in combination in order to obtain special effects, as described in Belgian Patent Specification No. 537,278 and in British Patent Specification No. 727,982.

The emulsions must be sufficiently sensitive in the blue region of the spectrum. Unsensitised emulsions in which the sensitivity is due to the intrinsic sensitivity of the silver halides are generally used for this purpose but the silver halide emulsions may also be sensitised to the blue region of the spectrum, for example by means of sensitisers of the kind described in German Offenlegungsschrift No. 1,808,041.

The emulsions may contain the usual stabilisers, for example homopolar compounds or salts of mercury containing aromatic or heterocyclic rings, such as mercaptotriazoles, simple mercury salts, sulphonic mercury double salts and other mercury compounds. Azaindenes are also suitable stabilisers, particularly tetra- and pentazaindenes, especailly those which are substituted with hydroxyl or amino groups. These compounds have been described in the article by Birr. Z. Wiss. Phot, 47, 2–27 (1952). Other suitable stabilisers include heterocyclic mercapto compounds, e.g. phenylmercapto tetrazole, quaternary benzothiazole derivatives, and benzotriazole.

The emulsions may be hardened in the usual manner, for example with formaldehyde or halogen substituted aldehydes containing a carboxyl group, such as mucobromic acid, diketones, methane sulphonic acid esters and dialdehydes.

The photographic layers may also be hardened with eposy, heterocyclic ethylene imine or acryloyl hardeners. Examples of such hardeners have been described, for example, in German Offenlegungsschrift No. 2,263,602 and in British Pat. No. 1,266,655. The layers may also be hardened by the process according to German Offenlegungsschrift No. 2,218,009 to produce colour photographic materials which are suitable for high temperature processing.

The photographic layers or colour photographic multi-layer materials may also be hardened with hardeners of the diazine, triazine or 1,2-dihydroquinoline series as described in British Pat. Nos. 1,193,290; 1,251,191; 1,306,544 and 1,266,655; French Patent Specification No. 7,102,716 or German Offenlegungsschrift No. 2,332,317. Examples of such harderners include diazine derivatives containing alkyl sulphonyl or aryl sulphonyl groups, derivatives of hydrogenated diazines or triazines, e.g. 1,3,5-hexahydrotriazine, fluoro-substituted diazine derivatives such as fluoro pyrimidines, esters of 2-substituted 1,2-dihydroquinoline- or 1,2-dihydroisoquinoline-N-carboxylic acids. Vinyl sulphonic acid hardeners and carbodiimide and carbamoyl hardeners are also suitable, for example those described in German Offenlegungsschriften Nos. 2,263,602; 2,225,230 and 1,808,685; French Pat. Specification No.

1,491,807, German Pat. Specification No. 972,153 and DDR Patent Specification No. 7,218. Other suitable hardeners have been described, for example, in British Pat. No. 1,268,550.

Suitable wetting agents which may be used according to the invention for incorporating the couplers have been described by Gerhard Gerwalek in "Wasch- und Netzmittel", Akademie-Verlag Berlin (1962). Examples of these wetting agents include the sodium salt of N-methyl-oleyl tauride, sodium stearate, the sodium salt of heptadecenyl benzimidazole sulphonic acid, sodium sulphonates of higher aliphatic alcohols, e.g. 2-methylhexanol sodium sulphonate, sodium diisooctyl sulphosuccinate, sodium dodecylsulphonate and the sodium salt of tetradecyl benzene sulphonic acid. Partially fluorinated or perfluorinated alkane carboxylic or alkane sulphonic acids or amides thereof are also suitable.

The materials according to the invention may be used for various purposes, for example as positive, negative or reversal materials.

The usual substrates used in known manner for the preparation of photographic materials may be used, for example foils of cellulose nitrate, cellulose acetate such as cellulose triacetate, polystyrene, polyesters such as polyethylene terephthalate or polyolefines such as polyethylene or polypropylene, baryta-coated paper substrates or a polyolefine laminated paper substrate, e.g. a polyethylene laminated substrate, or glass.

The advantageous properties of the couplers according to the invention will now be described with the aid of examples.

EXAMPLE (1) 2 moles of coupler No. 8 are dissolved in 3 ml of ethyl acetate and, after the addition of 0.5 g of dibutylphthalate, the solution is emulsified in known manner in 20 ml of a 5% gelatine solution at 60° C. which contains 0.16 g of dodecyl benzene sulphonic acid sodium.

The emulsion is then mixed with 85 g of a 7.5% gelatine solution which contains 1.93 g of silver bromide in a dispersed form, and the mixture is then diluted with water to the required casting viscosity.

When the mixture has been cast on a transparent substrate of cellulose triacetate, the material prepared in this way after drying is exposed behind a grey step wedge and cut up into several samples.

One sammple is stored in a heating cupboard for seven days at 57° C. and 34% relative humidity before it is photographically processed. The untreated samples are processed in a colour developer which contains the following substances in the given quantities per liter:
 3 g of benzyl alcohol
 2 g of $Na_2SO_3$
 5 ml of NaOH (10%)
 50 g of $Na_2CO_3$ sicc.
 1 g of KBr
 5 g of N'-ethyl-N'-β-methyl sulphonamidoethyl-2-methyl paraphenylene diamine
 2 g of sodium hexametaphosphate.

| Processing: | | |
|---|---|---|
| Development: | 12 min. | 20° C. |
| Washing: | 15 min. | 20° C. |
| Colour negative bleaching bath | 5 min. | 20° C. |
| Washing: | 5 min. | 20° C. |
| Fixing bath: | 5 min. | 20° C. |
| Washing: | 10 min. | 20° C. |

A compound according to German Offenlegungsschrift No. 2,433,812, which has the same structure but carries a different reliasable group, as represented by the following formula:

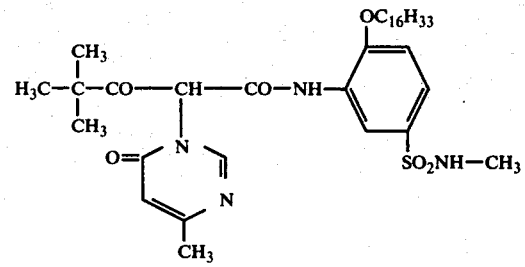

is used as comparison coupler and processed in the same manner. The results are compared in the following Table:

| Sample | Releasable group | Sensitivity DIN | $D_{max}$ | fog in heating cupboard | λmax |
|---|---|---|---|---|---|
| containing comparison coupler of German Offenlegungsschrift No. 2,433,812 | (structure) | Control | 2.0 | 58 | 444 |
| Coupler No. 8 | (structure) | +5.0 | 2.3 | 38 | 444 |

While the coupler according to the invention produces a dye of the same absorption maximum, it is distinguished by the substantially lower fog in the heating cupboard and increased maximum density and substantially higher sensitivity. The results obtained with other couplers according to the invention are summarised in the Table below. The following colour developer was used in this case:

Per Liter:
 4 g of sodium hexametaphosphate
 1.2 g of hydroxylamine hydrochloride
 2.75 g of N,N'-diethylamino-p-phenylene diamine 2 g of Na$_2$SO$_3$ sicc.
75 g of K$_2$CO$_3$
2.5 g of KBr

| Processing: | | |
|---|---|---|
| Development: | 8 min. | 20° C. |
| Washing: | 15 min. | 20° C. |
| Colour negative bleaching bath: | 5 min. | 20° C. |
| Washing: | 5 min. | 20° C. |
| Fixing bath: | 5 min. | 20° C. |
| Washing: | 10 min. | 20° C. |

Further examples

| Coupler | Releasible group | D$_{max}$ | fog in heating cupboard | λmax |
|---|---|---|---|---|
| 2 | | 2,7 | +16 | 434 |
| 3 | | 2.5 | +10 | 434 |
| 5 | | 2.8 | +16 | 440 |
| 9 | | 2.7 | +30 | 435 |
| 12 | | 2.9 | +22 | 432 |
| 13 | | 2.6 | +36 | 435 |

High maximum densities combined with very slight fogging due to storage in the heating cupboard and sensitivities at least equal to that observed with the 4-equivalent coupler are obtained in all cases. As is well-knowm, 4-equivalent couplers are characterised by comparatively high sensitivities.

We claim:

1. A light sensitive material comprising at least one silver halide emulsion layer and in close special relationship thereto a 2-equivalent yellow coupler which contains, in the coupling position, a nitrogen-containing group capable of being split off in the coupling reaction, wherein the improvement comprises the 2-equivalent coupler contained in the material is a compound of one of the following formulae:

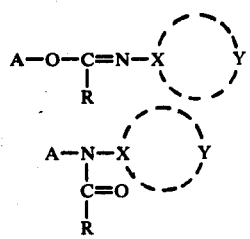

in which
X represents a ring nitrogen or ring carbon atom;
Y represents the ring members required to complete a saturated or unsaturated heterocyclic ring selected from the group consisting of the thiadizole, 1,2,3- and 1,2,4-triazole, tetrazole, thiazole, 1,2- and 1,3-diazole, pyrrole, triazine, pyridine and pyrimidine ring inclusive of those derivatives of said rings in which a benzene ring is condensed to the heterocyclic ring and inclusive of those derivatives of said rings in which the heterocyclic ring contains one or two keto groups on the ring;

R represents (1) alkyl, (2) aryl, (3) alkoxy or (4) a furyl or pyridyl group;

A represents the radical of an open-chain ketomethylene yellow coupler structure having a methylene group activated by two adjacent carbonyl groups and the radical being obtained by removal of a hydrogen from the activated methylene group.

2. Material as claimed in claim 1, in which the coupler radical A of the 2-equivalent coupler has the following formula:

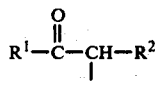

in which $R^1$ represents alkyl or aryl;
$R^2$ represents the group

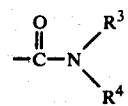

in which $R^3$ represents hydrogen or alkyl having 1 to 4 carbon atoms;

$R^4$ represents alkyl or phenyl which may be substituted with alkyl groups having from 1 to 18 carbon atoms, halogen, aryl, aralkyl, aroxy, sulfo, carboxyl, acyl, acyloxy, acylamino groups.

3. Material as claimed in claim 2 in which $R^1$ represents a tertiary butyl group or a phenyl group which may be substituted with halogen, alkoxy, acylamino, alkyl, aroxy, hydroxy, alkylamino, or dialkylamino groups.

* * * * *